(12) United States Patent
Salzbrenner et al.

(10) Patent No.: US 9,651,464 B1
(45) Date of Patent: May 16, 2017

(54) SPRING PERFORMANCE TESTER FOR MINIATURE EXTENSION SPRINGS

(71) Applicant: Sandia Corporation, Albuquerque, NM (US)

(72) Inventors: Bradley Salzbrenner, Albuquerque, NM (US); Brad Boyce, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 127 days.

(21) Appl. No.: 14/477,196

(22) Filed: Sep. 4, 2014

Related U.S. Application Data

(60) Provisional application No. 61/874,062, filed on Sep. 5, 2013.

(51) Int. Cl.
  *G01L 1/04* (2006.01)
  *G01N 3/26* (2006.01)
  *G01N 3/02* (2006.01)

(52) U.S. Cl.
  CPC .................................... *G01N 3/02* (2013.01)

(58) Field of Classification Search
  None
  See application file for complete search history.

(56) References Cited

U.S. PATENT DOCUMENTS

| | | | | |
|---|---|---|---|---|
| 3,675,479 A * | 7/1972 | Carlson | ................ | G01N 3/00 73/161 |
| 3,875,795 A * | 4/1975 | Haefele | ................ | G01N 3/00 73/161 |
| 5,033,298 A * | 7/1991 | Hueck | ................ | G01N 3/00 73/161 |
| 5,832,774 A * | 11/1998 | Smith | ................ | G01N 3/00 73/161 |
| 5,872,319 A * | 2/1999 | Bruns | ................ | G01L 1/042 73/862.641 |
| 6,128,950 A * | 10/2000 | Hoagland | ................ | G01N 3/08 73/161 |
| 6,931,941 B2 * | 8/2005 | Shelby | ................ | G01N 3/00 73/808 |
| 7,069,778 B1 * | 7/2006 | Strehler | ................ | G01N 3/00 33/535 |
| 7,971,331 B2 * | 7/2011 | Winkle | ................ | G01L 5/0038 29/407.01 |
| 7,992,612 B2 * | 8/2011 | Shelley | ................ | B30B 15/0094 156/351 |
| 8,151,638 B2 * | 4/2012 | Erlenkeuser | ................ | G01N 3/00 73/161 |
| 8,720,265 B2 * | 5/2014 | Lin | ................ | G01M 99/007 73/161 |

* cited by examiner

*Primary Examiner* — Daniel S Larkin
*Assistant Examiner* — Jermaine Jenkins
(74) *Attorney, Agent, or Firm* — Daniel J. Jenkins

(57) ABSTRACT

A spring performance tester and method of testing a spring are disclosed that has improved accuracy and precision over prior art spring testers. The tester can perform static and cyclic testing. The spring tester can provide validation for product acceptance as well as test for cyclic degradation of springs, such as the change in the spring rate and fatigue failure.

18 Claims, 3 Drawing Sheets

SPRING PERFORMANCE TESTER FOR MINIATURE EXTENSION SPRINGS

CROSS-REFERENCE TO RELATED APPLICATIONS

This application claims benefit of U.S. Provisional Patent Application No. 61/874,062, "SPRING PERFORMANCE TESTER", filed Sep. 5, 2013, which is incorporated by reference herein in its entirety.

GOVERNMENT RIGHTS

The Government has rights to this invention pursuant to Contract No. DE-AC04-94AL85000 awarded by the U.S. Department of Energy.

FIELD

The invention relates generally to parts testing, and more particularly to a multi-function spring tester for testing the compression and extension loads, deflections and rates of springs.

BACKGROUND OF THE INVENTION

Miniature coil wound springs are used in mechanical applications such as firing and failsafe devices, medical devices, compact electronic controls, precision instruments, firearms, pharmaceutical delivery devices, aerospace and marine components, and petro-chemical processes. Commercially available spring test systems lack sufficient force resolution or cyclic test capabilities for these miniature scale springs.

Traditional spring testers work on the basis of compressing (or extending) a spring to a known deflection and recording that force value. Then moving to second known deflection and recording that force value. This is done manually by a user and has no capability of automation or fatigue.

At this time, no spring tester has been developed that can accurately access the performance of miniature springs for quality assurance and product acceptance while at the same time measuring their fatigue performance.

A need remains, therefore, for a spring tester with improved accuracy and precision that can serve as a means for product acceptance and inspection while at the same time being capable of evaluating the cyclic degradation of springs, such as the change in the spring rate over time and how and when failure will occur.

SUMMARY OF THE INVENTION

According to an embodiment of the invention, a spring performance tester is disclosed that includes an actuator system and a spring positioning system. The actuator system includes an actuator, a linear distance measurement system and a first attachment point. The spring positioning system includes a load cell and a second attachment point. The load cell is capable of measuring the load placed upon a spring attached between the first and second attachment points; and wherein the actuator is capable of cycling the spring under compression and/or extension force.

According to another embodiment of the invention, a spring testing system is disclosed that includes a spring tester, a control system and an operation system. The spring tester includes an actuator and a spring positioning system. The actuator system includes an actuator, a linear distance measurement system and a first attachment point. The spring positioning system includes a load cell and a second attachment point. The load cell is capable of measuring the load placed upon a spring attached between the first and second attachment points. The actuator is capable of cycling the spring under compression and/or extension force. The control system provides the desired linear displacements for a test to the spring tester. The operation system comprises a data acquisition and processing unit.

According to another embodiment of the invention, a method of testing a spring is disclosed that includes zeroing a load cell, entering a nominal free length of a spring to be tested, loading a spring between grips, entering spring specifications into a control system, and testing the spring in static or fatigue mode and creating a data file.

DESCRIPTION OF THE INVENTION

The disclosed spring performance tester improves the accuracy and precision over prior art spring testers used to evaluate extension springs, and in particular, miniature extension springs. The spring tester may be used to evaluate static or fatigue spring characteristics. In an embodiment, a method is disclosed wherein the spring tester is used to evaluate cyclic degradation of springs, such as the change in the spring rate and fatigue failure. The spring tester can be used to evaluate extension and compression springs and provides a test platform that can evaluate the cyclic (fatigue) degradation of springs.

The term "spring" as used herein refers to any flexible component that can be axially loaded, such as, but not limited to mechanical coil springs produced by traditional coil winding techniques or helical cutting of raw stock material. For example, a spring may be, but is not limited to an extension spring, which responds or returns to an un-stretched shape when stretched open by a force and released, a compression spring, which responds or returns to an un-compressed shape when they are forced closed, or a combination extension/compression spring. The term "spring" does not refer to helical torsion springs, or other types of springs that are not loaded axially.

The term "miniature" as used herein refers to components having maximum dimension of less than one inch.

According to the present invention, the disclosed spring tester can perform "static" testing, wherein a spring is extended and/or compressed and the extension or compression force measured, and can also perform cyclic testing, wherein a spring is cyclically extended and/or compressed. The spring tester can deflect a spring back and forth between known deflections millions of times and record the force values throughout (fatigue testing). In an embodiment, the spring may have free length (free length is defined as the length of the spring in a relaxed or unstreched/uncompressed state ranging from 0.10 inches up to 1.0 inches and deflections from 20% to 200%.

The max dimension spring the tester can handle is limited by the max deflection of that spring. According to an embodiment, the spring tester can test a spring with a deflection smaller than 1 inch. According to another embodiment, the spring tester can test springs with deflections up to 3 inches if an actuator with larger throw is used. In an embodiment, the tester may be modular and able to accept a larger throw actuator if necessary.

Figure 1:
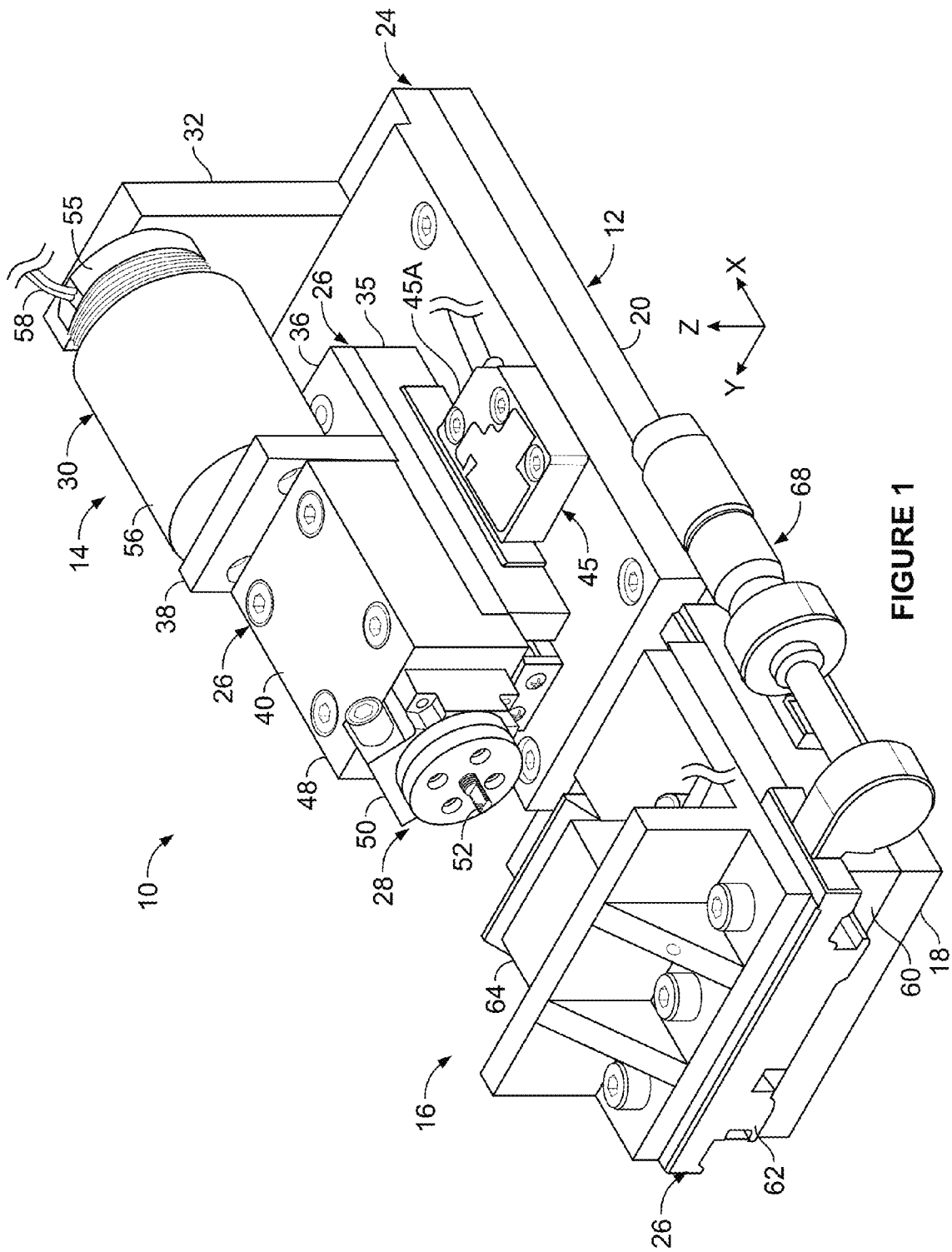
FIG. 1 is a perspective view of an embodiment of the spring tester.
Figure 2:
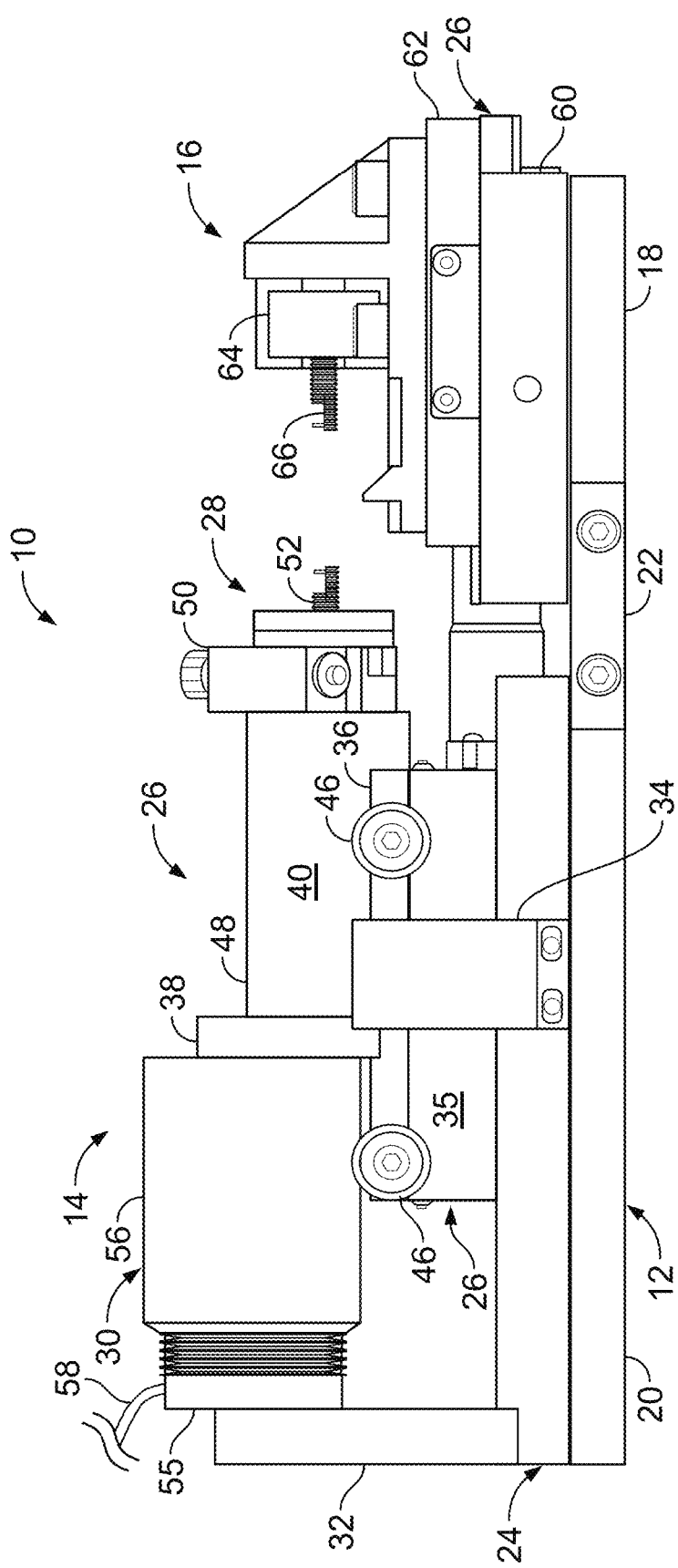
FIG. 2 is a side view of the spring tester of FIG. 1.
Figure 3:
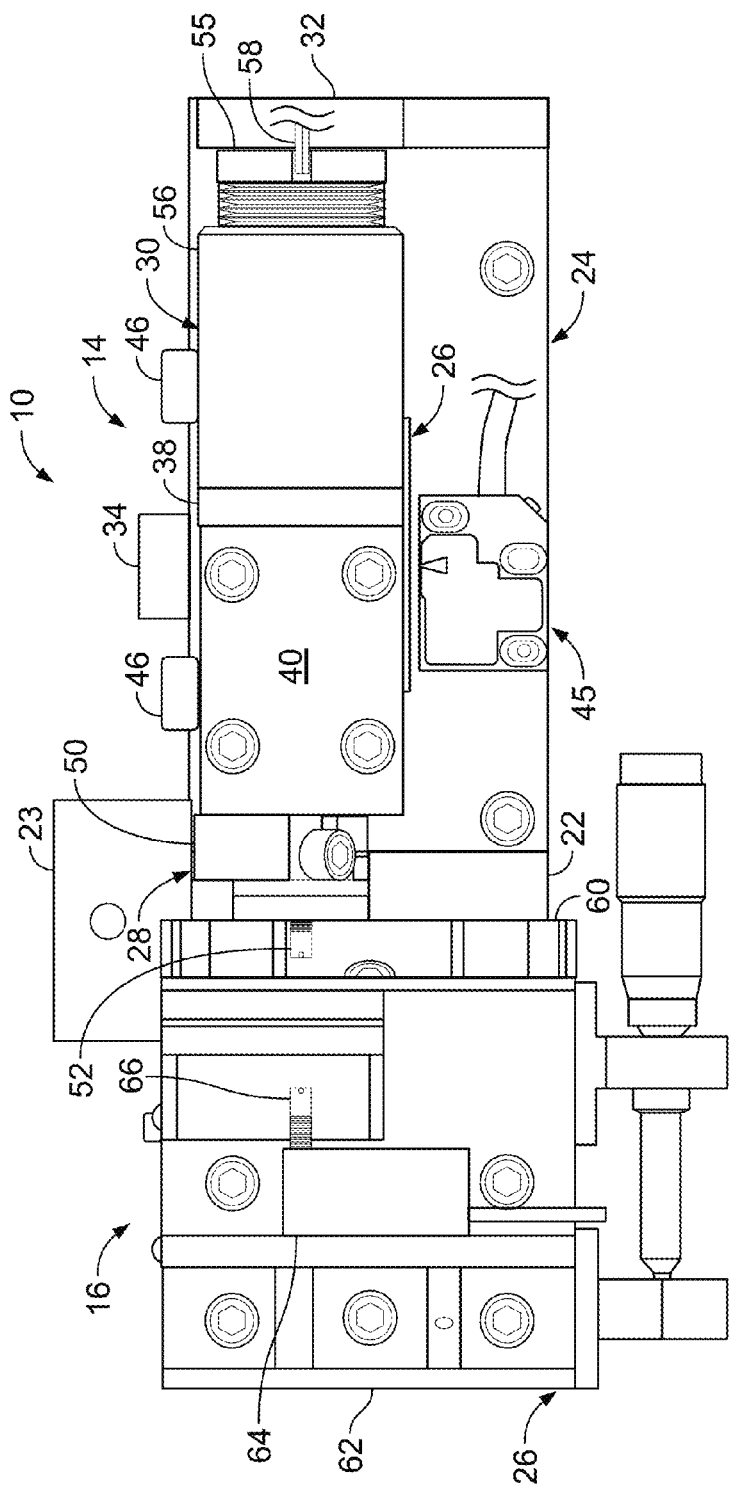
FIG. 3 is a top view of the spring tester of FIG. 1.

FIGS. 1-3 illustrate an embodiment of a spring tester 10 according to the invention. As can be seen in FIGS. 1-3, the spring tester 10 includes a base 12, an actuator system 14 and a spring positioning system 16. The base 12 includes a load measurement portion 18, an actuator support portion 20 and an interconnection portion 22. The base 12 includes an optional attachment portion 23. In another embodiment, the base 12 may include other attachment portions and/or points for accessories, such as, but not limited to lights, microscope cameras, additional distance measuring devices, and electrical probing devices.

The interconnection portion 22 attaches the load measurement portion 18 to the actuator support portion 20. The interconnection portion 22 may be changed to adjust the distance separating the load measurement portion 18 and the actuator support portion 20. In another embodiment, the base 12 may include one or more interconnection portions. In yet another embodiment, the interconnection portion 22 may not be present, and the load measurement portion 18 and the linear support portion 18 may be directly attached to one another. In yet another embodiment, the base 12 may be a single, solid unit.

The actuator system 14 includes an actuator system base 24, a slide system 26, a spring attachment system 28, and an actuator 30. The actuator system base 24 includes an actuator support 32 and a travel limiter 34. The actuator system base 24 is attached to the base 12. In another embodiment, the actuator support 32 may be part of or incorporated into the base 12. The actuator support 32 is attached to and supports the actuator 30. The travel limiter 34 is attached to the actuator support 32. In another embodiment, the travel limiter 34 may be part of or incorporated into the actuator support 32.

The slide system 26 includes a base 35, a slide portion 36, an actuator support 38 and a spring support 40. The slide system 26 further includes a linear distance measurement system 45. The base 35 is attached to the actuator system base 24. The slide portion 36 rests upon and is in contact with the base 35. The slide portion 36 moves or slides in the X axis as shown in FIG. 1, which is referred to as the linear direction. The slide portion 36 includes travel stops 46 that limit the distance, movement and travel of the slide portion 36 on the base 35 in the linear direction.

The slide portion 36 and/or base 35 may include ball bearings or air bearings between the slide portion 36 and the base 35 to reduce friction therebetween. In another embodiment, other friction reduction devices or methods may be used, such as, but not limited to Teflon supports and crossed roller or crossed cylinder sliders.

The linear measurement system 45 measures the amount of travel or distance of the slide system 26 in the linear direction. In this exemplary embodiment, the linear measurement system 45 is a linear encoder having a magnetic contact (not shown) embedded in the base 35. In another embodiment, the linear measurement system 45 may be, but is not limited to a linear variable differential transformer (LVDT), photoelectric distance-measurement device, cable-pull encoder, LED or LASER measurement sensor or inductive sensor. In an embodiment, the linear measurement system 45 provides feedback loop for the actuator 30. In such a manner, feedback may be used to accurately move the actuator to the desired position for spring testing. In an embodiment, the linear measurement system 45 may have a resolution of 1 micron or less.

In this exemplary embodiment, the slide measurement system is attached to the actuator system base 24. In another embodiment, the slide measurement system 45 may be attached to another portion of the spring tester 10. In yet another embodiment, the slide measurement system 45 may not be attached to the spring tester 10.

The actuator support 38 is attached to the slide portion 36. The actuator support 38 includes one or more attachment points (not shown) for attaching the actuator 30 to the slide system 26. The actuator points may be clips, fasteners or fastener portions capable of securing or attaching the actuator 30 to the actuator support 38.

The spring attachment system 28 is attached to the spring support 40. The spring attachment system 28 includes a rotary stage 50 attached to the base 48, and a first attachment device 52 attached to the rotary stage 50. The rotary stage 50 is adjustable and allows the attachment device 52 to be rotated around the linear direction and secured in that orientation. In such a manner, the rotary stage 50 allows for springs (not shown) with various spring terminal or end point alignment to be attached to the attachment device 52. In another embodiment, the rotary stage 50 may be omitted and the attachment device 52 may be directly attached to the base 48.

The attachment device 52 is attached to the rotary stage 50. In this exemplary embodiment, the attachment device 52 is a hook or grip having a projection capable of engaging a spring end point. In another embodiment, the attachment device 52 may be another device capable of securing a spring's end point to the spring support 40, such as, but not limited to clips, pins and other fasteners.

The actuator 30 is an electronic and/or magnetic device capable of rapid linear cyclic movement. The actuator 30 includes a base 55, a travel member 56 and an electrical/control connection 58. The base 54 is attached to the actuator support 32 of the actuator system base 24. The travel member 56 is in contact with the base 55 and is configured to cyclically travel in the linear direction. The travel member 56 can cycle over a distance of 1 inch. In another embodiment, the travel member 56 may cycle over a travel distance of 0.5 inches. In another embodiment, the travel member 56 may cycle over a travel distance of 2 inches. In another embodiment, the travel member 56 may cycle over a travel distance of 3 inches.

In this exemplary embodiment, the actuator 30 cycles the travel member 56 at a cycle rate of 2 hertz. In an embodiment, the actuator 30 may cycle the travel member 56 at a cycle rate up to 5 hertz. In an embodiment, the actuator 30 may cycle the travel member 56 at a cycle rate up to 10 hertz. In such a manner, the actuator 30 provides linear motion to stretch or compress the spring, In this exemplary embodiment, the actuator 30 is a voice coil, and the base 55 is permanent magnetic field assembly and the travel member 56 is a coil assembly. In another embodiment, the actuator 30 may be a voice coil linear actuator, servo hydraulic, electromechanical or piezoelectric actuator, or any other device capable of cyclic linear movement in a desired distance/cycle rate performance range.

The spring positioning system 16 includes a base 60, an adjustable positioning platform 62, a load cell 64, a second attachment device 66, and a position adjustment device 68. The base 60 is attached to the base 12. The adjustable positioning platform 62 is slideably connected to the base 60.

The position adjustment device 68 is attached to the base 60 and contacts the adjustable positioning platform 62. The position adjustment device 68 is a device capable of linearly moving the adjustable positioning platform. In such a manner, the distance between the first and second attachment devices may be adjusted. In this exemplary embodiment, the adjustable positioning device 68 is a micrometer, but in another embodiment, the adjustable positioning device 68 may be a micrometer, slide, or other positioning device cable of adjusting the position of the adjustable positioning platform 62.

The load cell 64 is attached to the adjustable positioning platform 62. The load cell 64 may be a force transducer, force sensor, or piezo force washer, or other force measurement system capable of converting mechanical load into an electrical signal. In an embodiment, the load cell 64 may provide 0.011 grams or less of force resolution.

The second attachment device 66 is attached to the load cell 64 in a manner that the load cell 64 can measure the amount of force applied to the second attachment device in either linear direction so that the load cell 64 can measure the amount of compressive or extension force applied to a spring attached to the first and second attachment devices. In this exemplary embodiment, the second attachment device 66 is a hook or grip having a projection capable of engaging a spring end point, similar to the first attachment device 52. In another embodiment, the attachment device 52 may be another device capable of securing a spring's end point to the spring support 40, such as, but not limited to clips, pins and other fasteners. In another embodiment, the second attachment device 66 may be different than the first attachment device 52.

In another embodiment, the spring positioning system 16 may further include a rotary stage between the second attachment device 66 and the adjustable positioning platform 62. In this embodiment, the rotary stage 50 may or may not be present.

Figure 4:
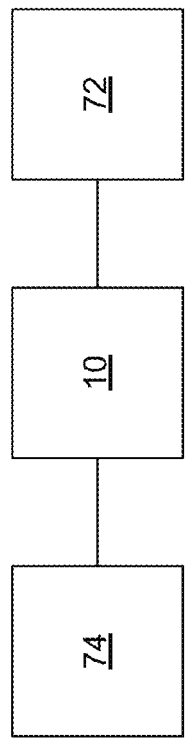
FIG. 4 is a schematic of an embodiment of a spring tester system according to the invention.

FIG. 4 illustrates an embodiment of a spring tester system 70 according to the invention. As can be seen in FIG. 4, the spring tester system 70 includes a spring tester 10, a control system 72, and an operation system 74.

The control system 72 includes a display, user interface, and software (not shown) for user input and data storage. In an embodiment, the control system 72 may be a laptop, desktop or networked computer system. The control system 72 provides the user with a way to communicate with the tester the desired displacements for the test. The control system also displays and records the data from the force transducer and position sensor.

The software is used to automate spring testing and record data. Such data may be used to serve as a means for product acceptance and inspection. The software provides real-time force readouts that give a user immediate feedback into how the spring is performing. Upon completion, the software performs calculations that tell the user whether or not the spring has passed or failed inspection.

The software may include fatigue and/or static spring testing software. The spring fatigue test software requires the user to input the known spring free length and the expected (required) spring properties. The standard specification for calling out spring properties is below and is how the values are to be entered into the program:

Load No. 1+/−tolerance 1 @ position no 1.
Load No. 2+/−tolerance 2 @ position no 2.

The user inputs the desired number of cycles and frequency to fatigue the spring. Upon execution, the program will begin fatigue testing the spring between position 1 and position 2 and raw data (force and displacement) will be recorded throughout the test. The average spring rate over one or more cycles is also recorded and saved to a data file to analyze the spring rate degradation over time. In an embodiment, the number of cycles may be four.

The spring fatigue tester uses software to automate fatigue testing and record data. The software also provides real-time view graphs that show the force-deflection curves that the spring is experiencing. This gives a user immediate feedback into how the spring is performing.

The static spring test software requires the user to input the known spring free length and the expected (required) spring properties as well. This is the same as with the fatigue software described above. With the static test software, the user does not have to enter any other data. Upon starting the test, the spring will be stretched to position 1 and the force value recorded. Then the spring will be stretched to position 2 and the force value recorded. The program will then run a calculation to determine whether or not the spring is within the defined tolerances as specified by the user and report a pass or fail message.

The spring static tester uses software to automate spring testing and record data to serve as a means for product acceptance and inspection. The software provides real-time force readouts that give the user immediate feedback into how the spring is performing. Upon completion, the software performs calculations that tell the user whether or not the spring has passed or failed inspection.

The operations system 74 is a system's data acquisition and processing unit. The system's operation system contains signal conditioning electronics to process the signals from the force transducer and linear encoder. The signals are unified and scaled to a +/−10 volt DC scale and sent to a data acquisition system (not shown and inside the operation system). The operations system 74 interfaces with the control system 72 via USB 2.0 to record and plot data. In another embodiment, the operations system 74 may interface with the control system 72 via wireless, serial, Ethernet, USB 3.0, or firewire. The operation system also houses a power supply and control unit for the voice coil actuator. This interfaces with the laptop via Ethernet and allows the user to input displacement values for the actuator. The values are processed in the operation system and appropriate voltages are sent to the actuator in order for movement to occur According to an embodiment of the invention, a method of fatigue testing a spring is disclosed. The method includes:
  Inputting the type of test, fatigue, into the control system;
  zeroing a force transducer;
  entering the nominal free length of the spring to be tested;
  loading a spring into the grips;
  entering the spring specifications as provided by the manufacturer of the spring; and
  testing the spring in fatigue mode and creating a data file.

Fatigue mode cycles the spring back and forth between two user assigned points.

The data file may include number of cycles, spring extension/compression force, amount (length) of extension/compression, spring rate, and percent of expected force at desired extension/compression.

The software may also determine a failure point (spring percent of expected force at desired extension/compression) of the spring as a function of cycles.

The results of fatigue testing can provide insight into how a spring performs over its lifetime; for example the degradation in spring rate and maximum and minimum force values as well as how long a spring can survive in certain conditions. These results are very important as miniature springs are used in applications such as biomedical devices, firing and failsafe devices, compact electronic controls, firearms, precision instruments, pharmaceutical delivery devices, petro-chemical processes and aerospace and marine components. A spring which could fail prematurely in these components could cause catastrophic damage.

According to another embodiment of the invention, a method of static testing a spring is disclosed. The method includes:

Inputting the type of test, static, into the control system;
zeroing a force transducer;
entering the nominal free length of the spring to be tested;
loading a spring into the grips;
entering the spring specifications as provided by the manufacturer of the spring; and
testing the spring in static mode and creating a data file.

Static mode slowly stretches the spring up to a user defined point and back to its free length. Testing the spring in static mode includes operating the actuator to provide linear motion to stretch or and/or compress the spring.

The data file may include spring extension/compression force, amount (length) of extension/compression, spring rate, and percent of expected force at desired extension/compression.

The results of static spring tests show whether or not a spring has been constructed to design specifications (max and min force values, spring rate, initial tension, etc). These results are very important as miniature springs are used in applications such as biomedical devices, firing and failsafe devices, compact electronic controls, firearms, precision instruments, pharmaceutical delivery devices, petro-chemical processes and aerospace and marine components. A spring being used in these components that does not conform to strict design specifications could cause catastrophic damage.)

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A spring testing device, comprising:
an actuator system comprising an actuator, a linear distance measurement system and a first attachment point; and
a spring positioning system comprising a load cell and a second attachment point;
wherein the load cell is capable of measuring the extension and compression load placed upon a spring attached between the first and second attachment points; and
wherein the actuator is capable of cycling the spring under compression and extension force.

2. The device of claim 1, wherein the actuator is a voice coil linear actuator.

3. The device of claim 1, wherein the load cell is a force transducer.

4. The device of claim 1, further comprising a linear encoder that provides feedback control for actuator position.

5. The device of claim 1, further comprising a rotary stage to vary the alignment of the first or second attachment points.

6. A spring testing system, comprising:
a spring tester comprising:
an actuator system comprising an actuator, a linear distance measurement system and a first attachment point;
a spring positioning system comprising a load cell and a second attachment point;
wherein the load cell is capable of measuring an extension and compression load placed upon a spring attached between the first and second attachment points; and wherein the actuator is capable of cycling the spring under compression and extension force;
a control system; and
an operation system;
wherein the control system provides the desired linear displacements for a test to the spring tester; and
wherein the operation system comprises a data acquisition and processing unit; and
wherein the actuator is capable of cycling the spring under compression and extension force.

7. The system of claim 6, wherein the control system comprises a display, a user interface, and software for user input and data storage.

8. The system of claim 6, wherein the control system displays and records data from the load cell and linear distance measurement system.

9. The system of claim 6, wherein the operation system further comprises signal conditioning electronics to process the signals from the load cell and linear distance measurement system.

10. The system of claim 6, wherein the actuator is a voice coil linear actuator.

11. The system of claim 6, wherein the load cell is a force transducer.

12. The device of claim 1, further comprising a linear encoder that provides feedback control for actuator position.

13. The system of claim 6, further comprising a rotary stage to vary the alignment of the first or second attachment points.

14. A method of testing a spring, comprising:
zeroing a load cell;
entering a nominal free length of a spring to be tested;
loading a spring between grips;
entering spring specifications into a control system; and
testing the spring in static or fatigue mode with an actuator capable of cycling the spring under compression and extension force and creating a data file comprising the compression or extension load placed upon the spring.

15. The method of claim 14, wherein the load cell is a force transducer.

16. The method of claim 14, wherein testing comprises providing feedback control to cycle the spring.

17. The method of claim 14, wherein the data file comprises spring rate and maximum and minimum force values.

18. The method of claim 14, wherein the data file comprises one or more values selected from a group consisting of spring extension/compression force, amount of extension/compression, spring rate, and percent of expected force at desired extension/compression.

\* \* \* \* \*